United States Patent [19]

Korhonen

[11] Patent Number: 5,752,959

[45] Date of Patent: May 19, 1998

[54] ROTATABLE CABLE DRUM WITH AUTOMATIC CABLE LOCK

[75] Inventor: Francis J. Korhonen, Negaunee, Mich.

[73] Assignee: Pioneer Laboratories, Inc., Marquette, Mich.

[21] Appl. No.: 705,135

[22] Filed: Aug. 29, 1996

[51] Int. Cl.[6] ............................................. A61B 17/56
[52] U.S. Cl. ........................................................ 606/103
[58] Field of Search .............................. 606/74, 103, 61, 606/86, 60, 205, 206, 207, 208, 209; 242/364.2, 364.1, 364, 396, 407

[56] References Cited

U.S. PATENT DOCUMENTS

| | | |
|---|---|---|
| 5,116,340 | 5/1992 | Songer et al. . |
| 5,415,658 | 5/1995 | Kilpela et al. . |
| 5,536,270 | 7/1996 | Songer et al. . |
| 5,607,429 | 3/1997 | Hayano et al. ............................ 606/74 |

Primary Examiner—Guy V. Tucker
Attorney, Agent, or Firm—Gerstman, Ellis & McMillin, Ltd.

[57] ABSTRACT

A rotatable drum for winding cable with an automatic cable lock. The rotatable drum comprises a rotatable shaft which has a first transverse aperture, and an outer drum member having an outer cable winding surface, which outer drum member is carried on the shaft and freely rotatable rotation therewith. The outer drum member defines a second transverse aperture which is positioned to align with the first transverse aperture in a first rotational position of the outer drum member. The two apertures can also be spaced in other rotational positions. Thus insertion of the cable end into the aligned first and second transverse apertures, plus rotation of the shaft to wind the cable about the outer drum member, can cause spontaneous locking of the cable between the first and second apertures by opposed walls of the respective apertures pinching against the cable.

8 Claims, 1 Drawing Sheet

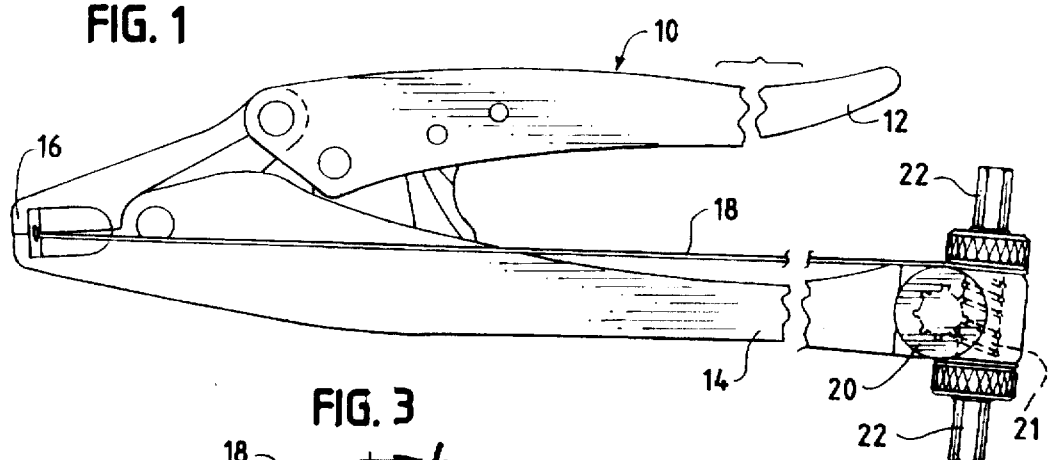
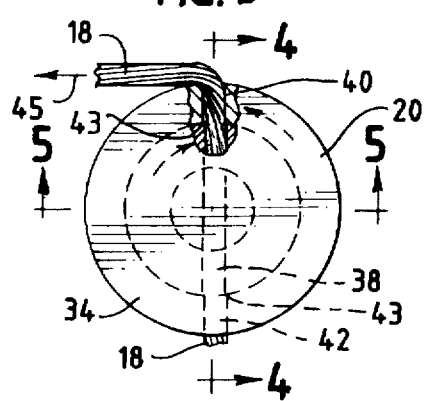
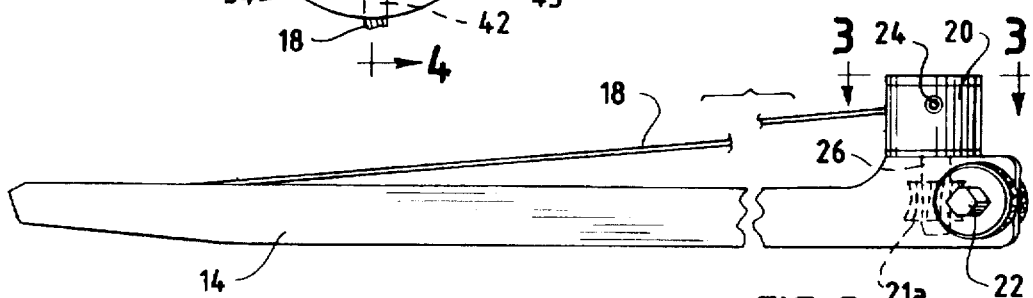
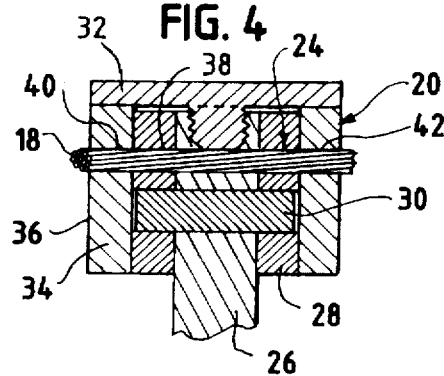
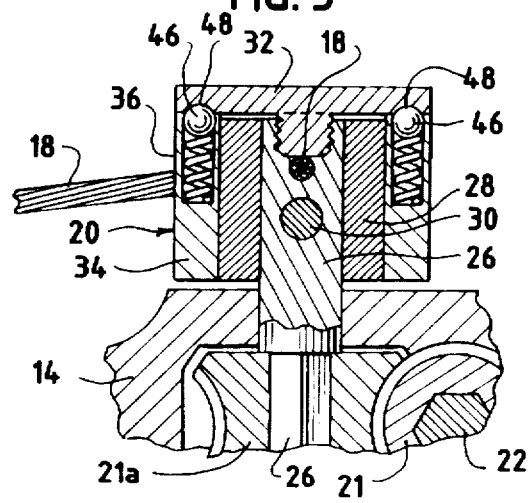

ROTATABLE CABLE DRUM WITH AUTOMATIC CABLE LOCK

BACKGROUND OF THE INVENTION

In Songer et al. U.S. Pat. Nos. 5,536,270, 5,116,340 and elsewhere, surgical cable systems for bone securance are disclosed, in which crimping pliers may carry a cable winding capstan which comprises a rotatable drum for winding the cable. Such a cable winding drum can define a transverse aperture into which the cable is passed, so that when the drum is wound, the cable is retained by frictional forces in and around the aperture, so that a desired tension can be placed on the cable by winding of the capstan.

Additionally, capstans and drums for cables are used in a multitude of different fields, where tension is placed on the cable by winding of the capstan or drum.

As one problem that arises, the cable often slips out of the transverse aperture rather than being frictionally captured and retained, so that successfully starting the winding of the cable can be difficult, particularly when the cable is short so that it does not extend a substantial distance through the transverse aperture.

By this invention, a rotatable drum for winding cable is provided, having an automatic cable lock which can grip even a relatively short piece of cable, to wind the cable on the drum and to exert any desired tension on the cable without slippage. As in the prior art, such a rotatable drum may be carried on the handle of cable pliers, or it may be used in any other desired mode of usage for the winding of cable. It is to be understood that the term "cable" is interpreted for purposes herein broadly, and may include wire, cord, and the like as well as multistrand cables.

DESCRIPTION OF THE INVENTION

By this invention a rotatable drum is provided for winding cable having an automatic cable lock. The drum, which is part of the whole capstan, may comprise a rotatable shaft, the shaft defining a first transverse aperture. An outer drum member is also provided, having an outer cable winding surface. The outer drum member is carried on the shaft in freely rotatable relation therewith. The outer drum member also defines a second transverse aperture which is positioned to align with the first transverse aperture in a first rotational position of the outer drum member. Also, the outer drum member can rotate to a second rotational position in which the second transverse aperture is rotationally spaced from the first transverse aperture.

Thus, insertion of a cable end into the aligned first and second transverse apertures, and rotation of the shaft to wind cable about the outer drum member, can cause spontaneous locking of the cable between the first and second apertures. This locking takes place as the cable is bent by the rotation of the first transverse aperture with the shaft. This causes rotational movement of the outer drum member, impelled by the bending of the cable, until one wall of the first transverse aperture and an opposed wall of the second transverse aperture pinch a portion of the cable together from opposite sides. From that time on, the pinching force is only increased as the tension on the cable is increased by adding winding torque, to provide a spontaneous, automatic cable lock.

This cable lock may take place irrespective of the number of windings of cable that are present on the drum or capstan, and irrespective of the fact that less than one complete winding of cable is present. It is the tension on the cable induced by the torque from the shaft that causes the cable to be pinched by the opposed walls of the respective apertures in a spontaneous manner.

Preferably, the first and second transverse apertures together extend completely through the drum, so that a cable may extend completely through the drum and project out the other end.

Also, the shaft preferably further defines a transversely enlarged, inner drum member which may be rigidly affixed by a pin or the like to the shaft, and around which the outer drum member is rotatably carried. The first transverse aperture also extends through the inner drum member, preferably completely through to provide a complete, open, transverse aperture.

It is also preferred for the shaft to carry a transversely extending end plate, which has at least one recess and preferably an opposed pair of them in a side that faces the shaft. The outer drum member carries at least one detent member positioned so that the detent member removably snaps into the recess in that rotational position of the outer drum member in which the first and second transverse apertures are aligned.

Thus, the user can initially snap the rotatable, outer drum member into the position of initial use, in which the two apertures are aligned so that, preferably, a transverse hole extends completely through the drum. For winding of a cable, the cable is placed through this hole comprising the two apertures, following which one simply rotates the shaft in conventional manner as the shaft rotates. The outer drum member rotates relative to the shaft to cause the two apertures to fall out of alignment to such an extent that opposed walls thereof pinch and retain the cable, as the winding process proceeds. As previously stated, this pinching action causes the spontaneous locking of the cable, with the retention force of the pinching action increasing as the torque on the shaft and the tension on the cable increases.

DESCRIPTION OF THE DRAWINGS

Referring to the drawings, FIG. 1 is a plan view of surgical pliers which carry the rotatable drum of this invention;

FIG. 2 is an elevational view of the surgical pliers of FIG. 1;

FIG. 3 is an enlarged, top plan view of the drum of FIG. 2, with a portion broken away, taken from line 303 of FIG. 2;

FIG. 4 is an enlarged, longitudinal sectional view, taken along line 4—4 of FIG. 3; and FIG. 5 is an enlarged, longitudinal sectional view of the same drum, taken along line 505 of FIG. 3.

DESCRIPTION OF SPECIFIC EMBODIMENTS

Referring to the drawings, a surgical crimper 10 is shown to be of pliers form, having a pair of pivoted handles 12, 14 with crimp-holding jaws 16 for securing a crimp and a section or sections of cable together in a manner similar to the cable securance disclosed in Songer et al. U.S. Pat. No. 5,116,340 or U.S. Pat. No. 5,536,270, among others. The crimping pliers and crimping system may be generally in accordance with the prior art, except as otherwise indicated herein.

Cable 18 may have a length extending rearwardly to rotatable drum 20 carried on a pliers handle, which may be conventionally rotated by means of rotatable pins 22 which are connected to rotatable drum 20 by a conventional worm gear system 21. Drum 20 defines a transverse aperture 24 through which cable 18 can pass.

In accordance with this invention, an automatic locking system is provided for the cable that passes through aperture 24, so that cable slippage is minimized or eliminated as drum 20 is rotated to exert tension on cable 18, as is commonly done in many surgical procedures in which the crimper may be used.

Turning to FIGS. 3 to 5, enlarged views of rotatable drum 20 are shown.

Drum 20 comprises a shaft 26 which connects to the conventional gears 21, 21a that mechanically and rotatably connect pins 22 and drum 20, so that the drum may be rotated.

Shaft 26 further defines a transversely enlarged, cylindrical inner drum member 28, which is secured to shaft 26 by a transverse pin 30 passing through respective apertures in shaft 26 and inner drum member 28.

Shaft 26 also carries a transversely extending end plate 32, conventionally secured to the end of shaft 26 in a rigid, co-rotating manner.

In accordance with this invention, an outer drum member 34, shown to be of cylindrical shape, is carried about shaft 26, as well as inner drum member 28. Outer drum member 34 has an outer, cylindrical cable winding surface 36, and is carried on and about shaft 26 in freely rotatable relation therewith, being generally closely dimensioned so that the bore of outer drum member 36 slides against the outer surface of inner drum member 28. Outer drum member 34 cannot move outwardly because of the presence of end plate 32, and it cannot move significantly inwardly because of the presence of arm 14 of the crimping pliers.

Transverse aperture 24 is shown in FIG. 4 to comprise a first transverse aperture 38 extending through shaft 26 and inner drum member 28, plus a second transverse aperture 40, 42, shown to be two separate aperture sections in this embodiment, which are positioned at opposed ends of transverse aperture 38 in the position shown in FIG. 4. However, it can be seen that outer drum member 34 can be rotated so that the transverse aperture portions 40, 42 can be rotationally spaced from transverse aperture 38. Also, the respective apertures may be partially spaced from each other, while they are in the condition of pinching and retaining the cable, as shown in FIG. 3. Note partial spacing 43, where portions 40, 42, do not exactly align with aperture portion 38.

FIG. 3 shows the action when a cable, extending through apertures 24, is subjected to winding action of the drum 20. The cable 18 naturally bends at the outer end of second aperture 40, the cable extends toward the jaws. As tension 45 is put on the cable, this forces outer drum 34 to rotate counterclockwise until respective, opposite side walls of aperture 38 and aperture 40 (42) pinch the cable in a forceful manner, the force depending upon the degree of tension (arrow 45) imposed on cable 18. Thus, drum 20 forcefully grips cable 18 in this circumstance, even if few loops of cable or even no complete loop of cable is present on the drum.

Thus, even a short length of cable can be reliably and strongly retained, so that the desired tension may be placed on the cable to achieve the desired surgical purpose. As described in the prior art, a torque wrench may be placed upon one of posts 22 to put a predetermined tension on cable 18.

With the desired tension on cable 18 being achieved with the assistance of locking drum of this invention, the surgical procedure involving in the cable may go forward in a conventional manner.

Outer drum 34 defines a pair of spring biased balls 46 to serve as detent members. End plate 32 defines a pair of snap-fit recesses 48 which are similarly distributed so that, at the rotational position of the components where transverse aperture 24 is completely formed by the aligned aperture portions 38, 40, 42, the balls of detent system 46 snap into recesses 48, so that the user can know the system is in proper rotational position for receiving a cable in aperture 24.

Thus a cable locking drum for surgical or any other desired use is provided, which greatly facilitates the easy application of tension onto a length of cable for any desired purpose, even when the length of cable is short so that it barely projects into or through aperture 24.

The above has been offered for illustrative purposes only, and is not intended to limit the scope of the invention of this application, which is as defined in the claims below.

That which is claimed:

1. A rotatable drum for winding cable having an automatic cable lock, which comprises:

a rotatable shaft, said shaft defining a first transverse aperture; and an outer drum member having an outer cable winding surface and carried on said shaft in freely rotatable relation therewith, said outer drum member defining a second transverse aperture which is positioned to align with said first transverse aperture in a first rotational position of said outer drum member, and to be spaced from said first transverse aperture in a second rotational position of said outer drum member, whereby insertion of a cable end into said aligned first and second transverse apertures and rotation of said shaft to wind cable about said outer drum member can cause spontaneous locking of the cable between the first and second apertures.

2. The rotatable drum of claim 1 in which said first and second transverse apertures together extend completely through said drum.

3. The rotatable drum of claim 1 in which said shaft further defines a transversely enlarged, inner drum member which is rigidly affixed to said shaft and around which said outer drum member is rotatably carried, said first transverse aperture extending through the inner drum member.

4. The rotatable drum of claim 1 in which said shaft carries a transversely extending end plate having at least one recess in a side that faces the shaft, said outer drum member carrying at least one detent member positioned so that the detent member removably snaps into the recess in that rotational position of the outer drum member in which the first and second transverse apertures are aligned.

5. Surgical pliers having a handle which carries the rotatable drum of claim 1.

6. A rotatable drum for winding cable having an automatic cable lock, which comprises:

a rotatable shaft, said shaft defining a first transverse aperture extending completely through said shaft; and an outer drum member having an outer cable winding surface and carried on said shaft in freely rotatable relation therewith, said outer drum member defining a second transverse aperture extending completely through said outer drum member, said second transverse aperture being positioned to align with said first transverse aperture in a first rotational position of said outer drum member, and to be spaced from said first transverse aperture in a second rotational position of said outer drum member, said shaft further defining a transversely enlarged, inner drum member which is rigidly affixed to said shaft and around which said outer drum member is rotatably carried, said first transverse aperture extending completely through said inner drum member, whereby insertion of a cable end into said aligned first and second transverse apertures and rotation of said shaft to wind cable about said outer drum member can cause spontaneous locking of the cable between the first and second apertures.

7. The rotatable drum of claim 6 in which said shaft carries a transversely extending end plate having at least one recess in a side that faces the shaft, said outer drum member carrying at least one detent member positioned so that the detent member removably snaps into the recess in the rotational position of the outer drum member in which the first and second transverse apertures are aligned.

8. Surgical pliers having a handle which carries the rotatable drum of claim 7.

* * * * *